United States Patent [19]

Newman et al.

[11] Patent Number: 4,526,449

[45] Date of Patent: Jul. 2, 1985

[54] OPTICAL SYSTEM FOR ILLUMINATED VIEWING INSTRUMENTS

[75] Inventors: Richard W. Newman, Auburn; William C. Moore; Byron A. Richards, both of Skaneateles, all of N.Y.

[73] Assignee: Welch Allyn Inc., Skaneateles, N.Y.

[21] Appl. No.: 408,631

[22] Filed: Aug. 16, 1982

[51] Int. Cl.$^3$ .................................................. A61B 3/14
[52] U.S. Cl. ..................................... 351/205; 351/206
[58] Field of Search ................. 351/205, 214, 218, 221

[56] References Cited

U.S. PATENT DOCUMENTS 1,281,136  6/1916  Clement .......................... 351/205 O
3,417,754  12/1968  Smart ............................... 351/205 X Primary Examiner—Rodney B. Bovernick
Attorney, Agent, or Firm—Bruns and Wall

[57] ABSTRACT

An optical system for illuminated viewing instruments comprising a light source lamp having an arcuate filament and a coacting mirror having an arcuate viewing passage in its upper edge. The optics of the system operate to focus the image of the filament on the mirror in concentric relation to the arcuate viewing passage whereby the axis of the reflected filament light and the viewer's line of sight are nearly coincident. In order to have all of the curved filament in focus on the mirror, the filament is tilted or disposed at an oblique angle to the longitudinal axis of the lamp. The optical system of the invention also permits use of a fixation pattern and provides the means for precisely focusing the pattern on the fundus of the patient's eye.

10 Claims, 10 Drawing Figures

Physician    Patient

OPTICAL SYSTEM FOR ILLUMINATED VIEWING INSTRUMENTS

BACKGROUND OF THE INVENTION

This invention relates generally to optical systems, and has particular reference to a novel optical system for illuminated viewing instruments. More specifically, the optical system of the invention is adapted for use in electrically illuminated diagnostic instruments such as ophthalmoscopes and the like.

In illuminated diagnostic instruments used in the examination of restricted body passages or other small openings, it has always been difficult to construct the instrument so that the viewer's line of sight substantially coincides with the beam of light emitted by the instrument. This has been particularly true of eye instruments such as ophthalmoscopes where the pupil provides the only natural opening through which the interior of the eye can be observed.

Even when dilated, the pupil is still a relatively small opening and there are many times when the fundus of the eye must be examined but dilation is not possible. Thus, the eye can only be dilated with caution when the patient is on medication for glaucoma, or when the patient is a baby or small child, and in certain other situations such as an emergency when time may not permit dilation. As will be readily understood, if there is anything more than a small angular displacement between the light beam and viewer's sight line, the viewer will not be able to look at the center of the area being illuminated.

Heretofore, the optical systems of ophthalmoscopes utilized a prism for changing the direction of the illuminating beam from axial with respect to the instrument to normal so that it can be projected outwardly into the patient's eye. This is necessary in this type of instrument since it is not practical to try to mount the light source in the upper part of the instrument in line with the patient's eye. Since the viewer cannot see through the prism, his line of sight must be just over its top and this means that the light from the light source must be made to emerge from the prism as close to the top as possible so that it almost coincides with the line of sight. This requires a precision prism, and even in the most precise instruments the optimum condition of having the line of sight and light beam coincide can never be attained.

At the present time, most ophthalmoscopes utilize a first surface mirror rather than a prism for changing the direction of the illuminating beam. In the majority of instrument designs this has reduced the angular displacement between the light beam and viewer's sight line but a further reduction is still needed, particularly when the pupil cannot be dilated. With the mirrors in present use, the viewer's line of sight still must be over the top.

SUMMARY OF THE INVENTION

In the invention disclosed herein improvements have been made to an optical system for an ophthalmoscope which enable the viewer's sight line and the illuminating beam to be nearly coincident. The improvements include a light source lamp having an arcuate filament and a coacting mirror having an arcuate viewing passage in its upper edge. The optics of the system operate to focus the image of the filament on the mirror in concentric relation to the arcuate viewing passage whereby the axis of the reflected filament light and the viewer's line of sight are nearly coincident.

In order to have all of the curved filament in focus on the mirror, the filament is tilted or disposed at an oblique angle to the longitudinal axis of the lamp, as will be described in more detail hereinafter. The optical system of the invention also permits use of a fixation pattern and provides the means for precisely focusing the pattern on the fundus of the patient's eye.

When the patient's pupil cannot be dilated, the coacting arcuate filament and arcuate viewing passage in the mirror enable the physician to look through the passage whereby his line of sight and the reflected light beam (axis of illumination) are nearly coincident. When the pupil can be dilated, the physician may look over the top of the mirror in the conventional way because this will enable more of the light reflected from the patient's eye to come back into the physician's eye.

The closest prior art known to the applicants is represented by U.S. Pat. No. 2,823,666 granted Feb. 18, 1958 to C. S. Hallpike et al and British Pat. No. 799,812 (8-1958) to Zeiss. The Hallpike patent discloses an otoscope type instrument having a lamp with a semi-circular filament and a mirror with a central viewing aperture. The patent also discloses means for producing an image of the filament on the mirror in concentric relation to the aperture. The purpose of the Hallpike instrument is to flood general illumination on the field being examined; it is incapable of producing an in-focus fixation pattern on the field because of a problem with the viewing aperture. On the one hand, the aperture should be as large as possible to get as much light as possible back into the physician's eye. On the other hand, the aperture should be as small as possible so that the filament image can be as close to a point source as possible so that the fixation pattern will be in exact focus. Unfortunately, there is no happy medium.

The Zeiss patent discloses an instrument for flooding a substantial amount of light onto the retina for photographic purposes. The principal objective of Zeiss is to eliminate corneal reflex back into the physician's eye or the photographic lens. However, the Zeiss instrument has the same aperture problems as Hallpike and its optical system would be unsuitable for achieving the objectives of the ophthalmoscope of the present invention.

The following additional patents are believed to be pertinent to the present invention: U.S. Pat. Nos. 669,949; 1,235,474; 1,461,367; 1,791,604; 2,301,185; 2,823,666 and 3,146,775; also British Pat. No. 782,318 (9-1957) to Oculus and French Patent of Addition No. 70,397 (11-1958) to Dudragne.

DESCRIPTION OF THE PREFERRED EMBODIMENT

Figure 1A:
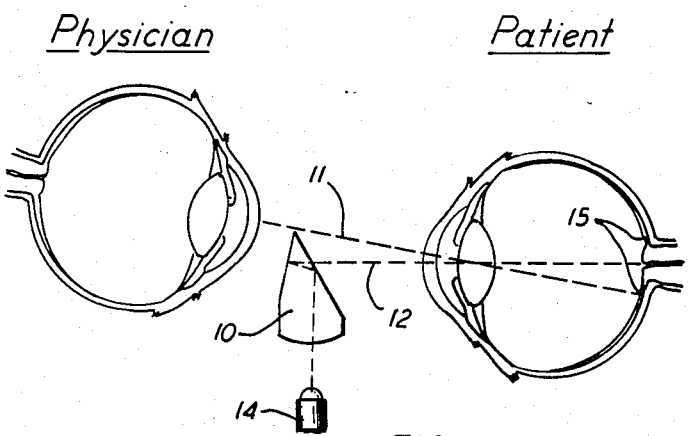
FIGS. 1A and 1B illustrate diagrammatically and in a simplified manner prior art ophthalmoscope optical systems.
Figure 2:
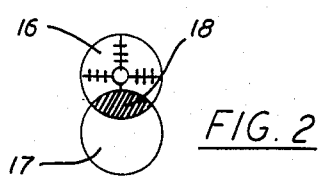
FIG. 2 is a diagrammatic illustration of the illuminated area and the viewed area on the fundus of the patient's eye using the optical system of FIG. 1A.

Having reference now to the drawings, the optical system of the invention will be described with particular reference to an ophthalmoscope although it will be apparent as the description proceeds that the system can also be advantageously used with various other types of instruments and devices. In the prior art illustrated by FIG. 1A, wherein the ophthalmoscope employs a prism 10, it can be seen that the physician's viewing axis 11 over the top of the prism and the illumination axis 12 derived from lamp 14 are not coincident but rather are diverging at the back or fundus 15 of the patient's eye. This angular displacement between the two axes at the fundus 15 will result in a pattern as shown in exaggerated form in FIG. 2 wherein the illuminated area 16 is above the area 17 viewed by the physician so that only the shaded overlapping portion 18 of the two areas is seen by the physician as being clearly illuminated.

Figure 1B:
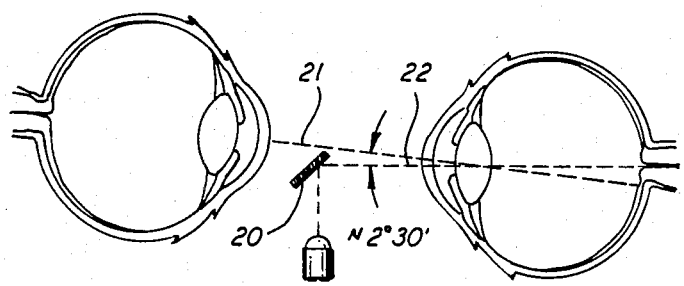

In the prior art illustrated by FIG. 1B, the ophthalmoscope utilizes a mirror 20 rather than a prism. With the mirror, the image of the lamp can be brought closer to the top of the mirror and the physician's viewing axis 21 and the illumination axis 22 are more -nearly coincident, the angle between the axes being two degrees and thirty minutes in the example shown. This is an improvement over the prism but for an undilated pupil the results are still not entirely satisfactory because the physician cannot see all of the illuminated area.

Figure 1C:
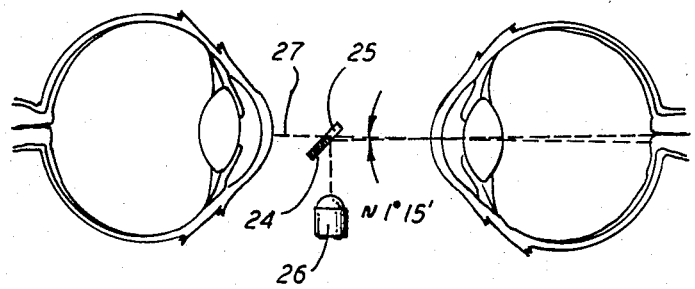
FIG. 1C is a view corresponding to FIGS. 1A and 1B but illustrating the optical system of the present invention.

FIG. 1C diagrammatically illustrates the optical system of the invention wherein the mirror 24 has a viewing passage 25 in its upper edge through which the physician can sight. This, coupled with an arcuate filament in lamp 26, as will be described in more detail hereinafter, causes the physician's viewing axis 27 and the illumination axis to be almost coincident as shown. Here, the angle between the axes is only one degree and fifteen minutes and the physician is able to see substantially all of the illuminated area.

Figure 3:
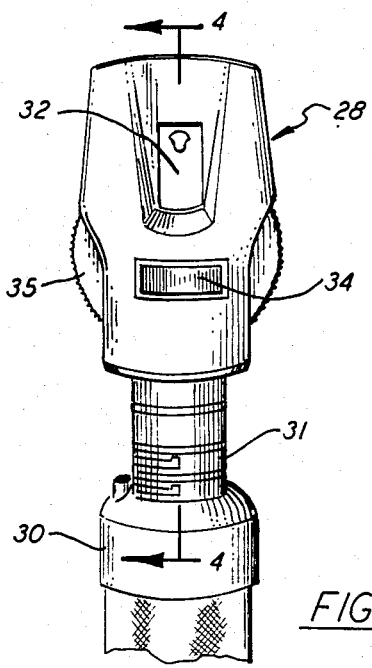
FIG. 3 is a fragmentary front elevation of an ophthalmoscope embodying the present invention.

With reference to FIG. 3, the ophthalmoscope of the invention, generally indicated at 28, is releasably secured to a conventional battery handle 30. A light source such as a lamp bulb (not shown in FIG. 3) is normally mounted inside the hollow stem 31 of the ophthalmoscope, current being supplied to the bulb by batteries located in the handle 30. Light is emitted from ophthalmoscope 28 into the patient's eye through aperture 32. The ophthalmoscope includes an aperture selection disc 34 and a conventional lens selection disc 35.

Figures 4, 5:
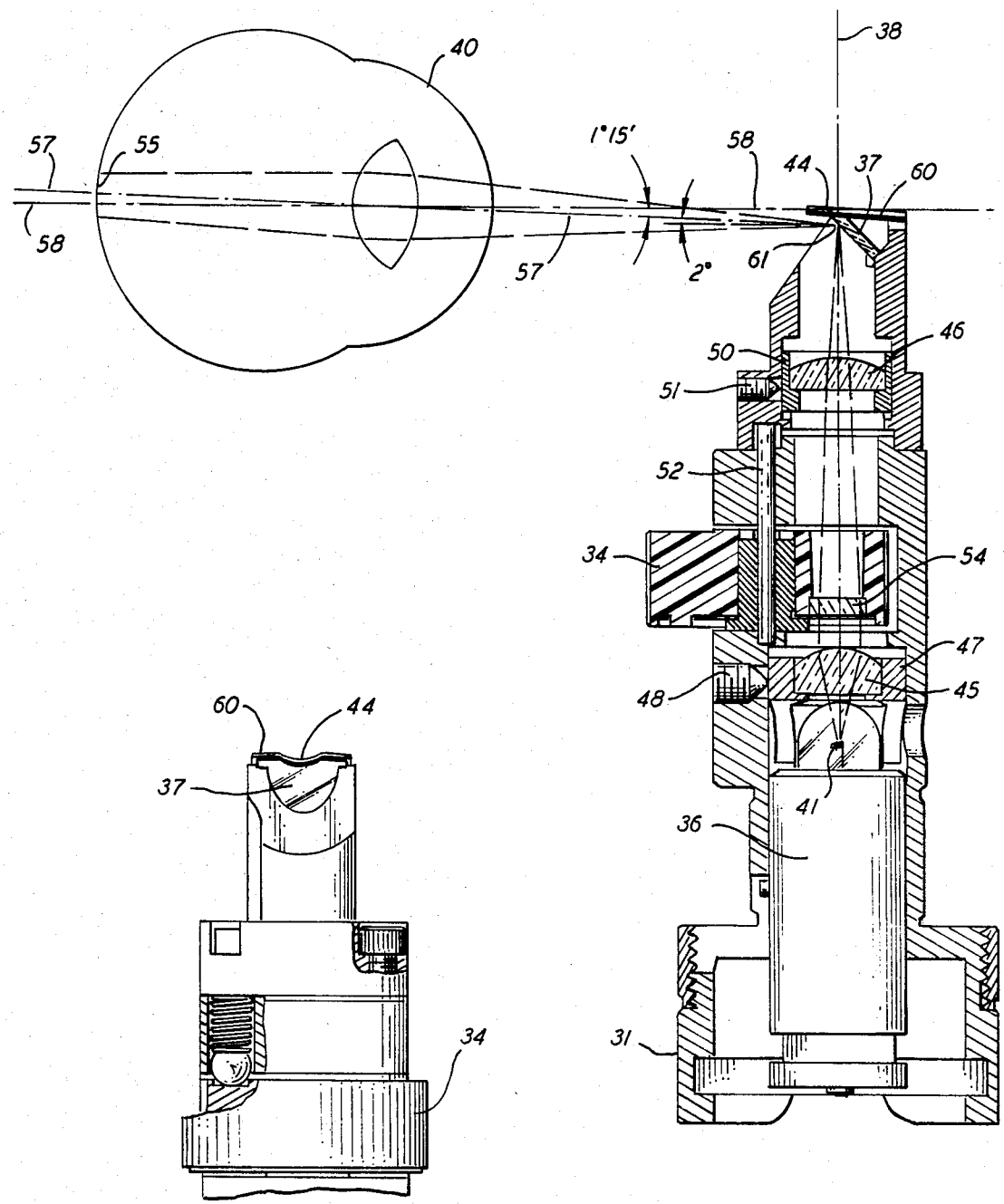
FIG. 4 is an enlarged, vertical sectional view of the optical system of the ophthalmoscope taken substantially on line 4—4 of FIG. 3, the light ray paths and patient's eye also being shown and the outer casing of the instrument being omitted.
FIG. 5 is a view corresponding to FIG. 4 but taken at substantially right angles thereto.

Reference is now made to FIGS. 4–8 which illustrate the details of the optical system, the outer casing of the ophthalmoscope being omitted in FIGS. 4 and 5. As noted above, the light source in the form of lamp 36 is mounted in the stem 31 which is adapted to be releasably connected to the battery handle 30, FIG. 3. Light rays from the lamp pass upwardly through an optical system, to be described, to a front surface mirror 37 that is angularly offset from the vertical axis 38 of the ophthalmoscope approximately 46°. The mirror alters the direction of the light rays or illuminating beam so that they project outwardly from the instrument into the eye of the patient generally indicated at 40 in FIG. 4.

Figure 6:
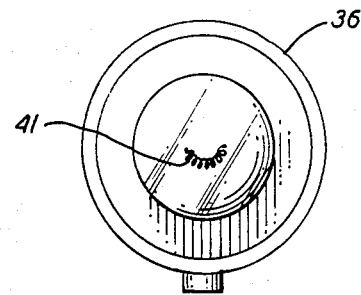
FIG. 6 is an enlarged top plan view of the light source lamp.
Figure 7:
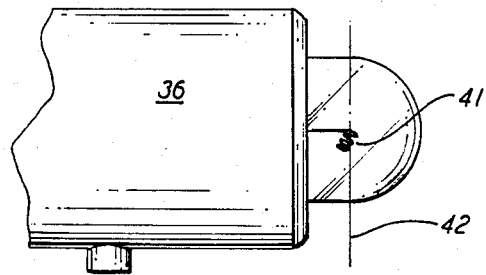
FIG. 7 is a fragmentary side elevation of the lamp.
Figure 8:
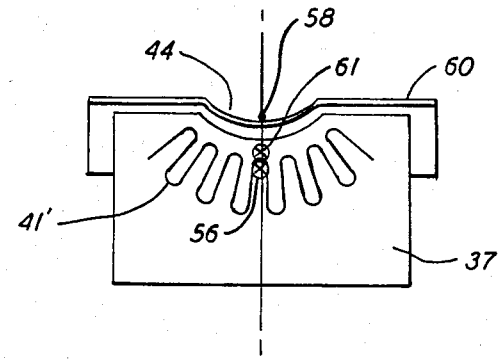
FIG. 8 is an enlarged front elevation of the mirror and its hood.

In accord with the invention, the filament 41 for the lamp 36 has an arcuate configuration as best shown in FIGS. 6 and 8. An image 41' of this filament is focused by the optical system on the mirror 37, FIG. 8. However, in order to have the entire curved filament in focus on the mirror the plane of the filament must be tilted or angularly offset from a plane 42 that is normal to the longitudinal axis of the lamp as best shown in FIG. 7. In a preferred embodiment of the invention, this angular offset is in a 15°–20° range.

Mirror 37 is provided with an arcuate viewing passage 44, FIGS. 5 and 8, at the approximate mid-point of its upper edge and the filament image 41' is focused on the mirror so that it is substantially concentric with the viewing passage as best shown in FIG. 8. Precise focusing of the filament image on the mirror is achieved by the optical system which includes a condensing lens 45 and objective lens 46 whose positions on the vertical or longitudinal axis 38 of the ophthalmoscope are factory adjusted to obtain the desired focus. To this end, the condensing lens 45 is mounted in an axially adjustable collar 47 whose adjusted position is maintained by a set screw 48. Similarly, the objective lens 46 is mounted in an axially adjustable collar 50 that is maintained in adjusted position by a set screw 51.

The aperture selection disc 34, FIGS. 4 and 5, is interposed between the condensing and objective lenses 45 and 46 and turns on a shaft 52 to bring various patterns, such as slit and fixation patterns, into registry with the optical axis which coincides with the previously mentioned vertical or longitudinal axis 38. In the illustrated embodiment of the invention, a fixation pattern is shown at 54 and this pattern is focused by the optical system on the fundus of the patient's eye at 55.

Because the filament 41 is arcuate, its centroid is located above the neutral axis of the filament as shown at 56 in FIG. 8. The centroid of a rectangular filament as was typically used in prior art ophthalmoscopes was located right on the neutral axis. The optical axis 38 meets the mirror 37 at point 61 very close to the filament centroid, FIG. 8, and is reflected by the mirror as the axis of illumination 57, FIG. 4. When the ophthalmoscope is in an exact vertical position, the axis of illumination is 2° above horizontal as indicated.

When the physician looks through the mirror viewing passage 44, FIGS. 4 and 8, his line of sight or viewing axis will be at 58 and from FIG. 8 it can be seen that the viewing axis and filament centroid are very close to one another. This is also shown in FIG. 4 where it can be seen that at the fundus 55 of the patient's eye there is very little divergence between the axis of illumination 57 and the physician's viewing axis 58 with the result that the physician will see substantially all of the illuminated fixation pattern, for example, that is focused on the fundus.

From FIGS. 4, 5 and 8, it will be seen that the mirror 37 is provided with a hood 60 that minimizes reflection back into the physician's eye. This hood conforms to the upper edge of the mirror following the curvature of the arcuate viewing passage 44 as best shown in FIG. 8.

In determining the curvature of the filament 41 and viewing passage 44, a number of factors must be considered. Thus, as the curvature of the filament increases, its centroid will get higher and therefore closer to the viewing axis. However, if the radius of the filament, and thus the viewing passage, is too small not enough light will get back to the physician. If, on the other hand, the curvature of the filament is too great it will not act as a point source and a pattern such as a fixation pattern may not be in exact focus on the fundus. The curvature of the filament and passage are therefore such that sufficient light gets back to the physician while keeping the centroid of the illuminated area of the filament as high as possible.

While emphasis has been placed upon the physician's use of the viewing passage 44, the optical arrangement described still permits the viewer to look over the top of the mirror in the conventional manner with improved results. This is an important advantage of the invention because it enables effective use of the instrument with either an undilated or dilated pupil. The invention has been described as utilizing an arcuate filament as the light source. However, it will be understood that this filament could easily be replaced by a fiber optic bundle having the same arcuate configuration which bundle would then serve as the light source.

From the foregoing description it will be apparent that the invention provides an improved optical system for viewing instruments that has a number of important advantages over the prior art. As will be understood by those familiar with the art, the invention may be embodied in other specific forms without departing from the spirit or essential characteristics thereof.

We claim:

1. An optical system comprising a light source having an arcuate filament, light reflecting means spaced from the light source and disposed at an oblique angle to the longitudinal axis thereof, the light reflecting means having a relatively small arcuate viewing passage formed in one edge thereof, and means forming a part of the optical system to project light rays from the light source onto the reflecting means in an in focus arcuate image that is close to and substantially concentric with the viewing passage.

2. An optical system as defined in claim 1 wherein the light reflecting means is a generally rectangular plate, the arcuate viewing passage being in the upper edge of said plate.

3. An optical system as defined in claim 1 wherein the light source filament lies in a plane that is disposed at an oblique angle to the longitudinal axis of the light source.

4. An optical system as defined in claim 1 wherein the system forms a part of an ophthalmoscope and the light rays projected onto the light reflecting means are reflected thereby into a patient's eye to illuminate the fundus of the eye.

5. An optical system as defined in claim 4 wherein the system includes a fixation pattern together with means for focusing the pattern image on the fundus of the eye.

6. In an optical system for use in electrically illuminated medical instruments, a light source in the form of a lamp having an arcuate filament, a mirror spaced from the light source and disposed at an oblique angle to the longitudinal axis thereof, the mirror having a viewing passage formed by an arcuate recess in its upper edge, means forming a part of the optical system for projecting light rays from the lamp filament onto the mirror in an in focus arcuate image that is close to and substantially concentric with the viewing passage, and a fixation pattern in the optical system together with means for focusing the pattern image on the fundus of the eye.

7. An optical system as defined in claim 6 wherein the lamp filament lies in a plane that is disposed at an oblique angle to the longitudinal axis of the lamp.

8. An optical system as defined in claim 6 wherein the system forms a part of an ophthalmoscope and the light rays projected onto the mirror are reflected thereby into a patient's eye to illuminate the fundus of the eye.

9. In an ophthalmoscope, an optical system comprising a light source capable of emitting an arcuate pattern of light rays, the light emitting surface of the light source lying in a plane that is disposed at an oblique angle to the longitudinal axis of the ophthalmoscope, a mirror spaced from the light source, the mirror being positioned in aligned but obliquely disposed relation to the longitudinal axis of the ophthalmoscope, the mirror having an arcuate viewing passage in its upper edge for the physician using the ophthalmoscope, and optical means positioned between the light source and mirror including lenses and a fixation pattern, the lenses being arranged to project the light rays from the light source onto the mirror in an in focus arcuate image that is close to and concentric with the viewing passage whereby the physician's line of sight through the passage is substantially coincident with the illumination axis of the light source rays reflected by the mirror, the reflected rays operating to illuminate the fundus of a patient's eye and focus image of the fixation pattern thereon.

10. An optical system as defined in claim 9 wherein the lenses include adjustably mounted condensing and objective lenses, proper adjustment of the lens positions permitting the light source filament to be precisely focused on the mirror.

* * * * *